United States Patent [19]

Branstetter et al.

[11] Patent Number: 5,216,598
[45] Date of Patent: Jun. 1, 1993

[54] SYSTEM FOR CORRECTION OF TRENDS ASSOCIATED WITH PULSE WAVE FORMS IN OXIMETERS

[75] Inventors: Ronald L. Branstetter; Reuben W. Edgar, both of San Antonio, Tex.

[73] Assignee: Colin Electronics Co., Ltd., Aichi, Japan

[21] Appl. No.: 774,147

[22] Filed: Oct. 15, 1991

Related U.S. Application Data

[63] Continuation of Ser. No. 417,084, Oct. 4, 1989, abandoned.

[51] Int. Cl.$^5$ ............................................. G06F 15/42
[52] U.S. Cl. ................................. 364/413.09; 128/637
[58] Field of Search .................... 364/413.09; 128/637, 128/653.1, 653.2, 653.3, 659, 660.01, 660.02

Primary Examiner—Gail O. Hayes
Attorney, Agent, or Firm—Oliff & Berridge

[57] ABSTRACT

A noninvasive optical oximeter measures oxygen saturation of arterial blood. A patient's arterial blood is illuminated with light at two different wavelengths and the intensity of the reflected light is sensed by a photodetector and an output signal is created in response thereto. The output signal is processed to form a ratio representing the AC component of the reflected light at each wavelength over the DC component. The oxygen saturation of the blood is calculated by correlating the quotient of these ratios with an oxygen reference curve uniquely representative of the blood oxygen characteristics of a particular patient. The pulse amplitude signals for the AC component at each wavelength are compensated for the effects of upward or downward trends and, therefore, the accuracy of the blood oxygen saturation calculation is significantly increased.

16 Claims, 2 Drawing Sheets

SYSTEM FOR CORRECTION OF TRENDS ASSOCIATED WITH PULSE WAVE FORMS IN OXIMETERS

This is a continuation of application Ser. No. 07/417,084 filed Oct. 4, 1989, now abandoned.

FIELD OF THE INVENTION

The present invention relates generally to monitoring equipment which can be used to estimate the degree of oxygen saturation of arterial blood. More specifically, the present invention provides an improved method and apparatus for calculating blood oxygen saturation which is resistant to the effects of signal artifacts.

BACKGROUND OF THE INVENTION

It is well known that hemoglobin and oxyhemoglobin have different optical absorption spectra and that this difference in absorption spectra can be used as a basis for an optical oximeter. Most of the currently available oximeters using optical methods to determine blood Oxygen saturation are based on transmission oximetry. These devices operate by transmitting light through an appendage such as a finger or an earlobe. By comparing the characteristics of the light transmitted into one side of the appendage with that detected on the opposite side, it is possible to compute oxygen concentrations. The main disadvantage of transmission oximetry is that it can only be used on portions of the body which are thin enough to allow passage of light. There has been considerable interest in recent years in the development of an oximeter which is capable of using reflected light to measure blood oxygen saturation. A reflectance oximeter would be especially useful for measuring blood oxygen saturation in portions of the patient's body which are not well suited to transmission measurements.

Various methods and apparatus for utilizing the optical properties of blood to measure blood oxygen saturation have been shown in the patent literature. Representative devices for utilizing the transmission method of oximetry have been disclosed in U.S. Pat. Nos. 4,586,513; 4,446,871; 4,407,290; 4,226,554; 4,167,331; and 3,998,550. In addition, reflectance oximetry devices and techniques are shown generally in U.S. Pat. Nos. 4,447,150; 4,086,915; and 3,825,342.

A theoretical discussion of a basis for the design of a reflectance oximeter is contained in "Theory and Development of a Transcutaneous Reflectance Oximeter System for Noninvasive Measurements of Arterial Oxygen Saturation," by Yitzhak Mendelson (Published Doctoral Dissertation), No. 8329355, University Microfilms, Ann Arbor, Mich. (1983). A theoretical discussion of the optical properties of blood is found in "Optical Scattering in Blood," by Narayanan R. Pisharoty, (Published Doctoral Dissertation), No. 7124861, University Microfilms, Ann Arbor, Mich. (1971).

Numerous other works have disclosed theoretical approaches for analyzing the behavior of light in blood and other materials. The following is a brief list of some of these references: "New Contributions to the Optics of Intensely Light-Scattering Materials, Part 1," by Paul Kubelka, Journal of the Optical Society of America, Volume 38, No. 5, May 1948; "Optical Transmission and Reflection by Blood," by R. J. Zdrojkowski and N. R. Pisharoty, IEEE Transactions on Biomedical Engineering, Vol. BME-17, No. 2, April 1970.

Generally, the pulse amplitude measured in a reflectance oximeter is less than one percent of the total reflected signal intensity. Therefore, inaccuracies in this measurement will cause the calculation of the blood oxygen saturation to be incorrect. Errors in the measurement of pulse amplitudes can occur when the levels of the waveforms have an upward or downward trend. When the average signal of the oximetry waveforms trend upward, the pulse amplitudes of the waveforms tend to be artificially small. Conversely, when the average signal of the oximetry waveforms trend downward, the pulse amplitudes of the waveforms tend to be artificially large. Prior systems tend to measure the pulse amplitudes of the waveform inaccurately when the levels of the waveforms have an upward or downward trend. As a result, the calculation of blood oxygen saturation for these pulses is incorrect. The method and apparatus of the present invention overcomes these difficulties, as described in greater detail below.

SUMMARY OF THE INVENTION

The present invention provides a noninvasive oximeter which is capable of providing accurate indications of a patient's blood oxygen saturation. In the preferred embodiment of the present invention, the oxygen saturation of a patient's arterial blood is determined by a noninvasive optical technique which takes advantage of differences in the absorption spectra of hemoglobin and oxyhemoglobin.

In its simplest form, the invention comprises an optical sensor including means for illuminating the patient's arterial blood with light at two different wavelengths, means for measuring the intensity of the detected light after contact with the blood and means for correlating the intensity of the light reflected with an oxygen saturation reference curve to determine the oxygen saturation of the patient's blood. One of the sources of light is at a wavelength for which the absorption coefficients of hemoglobin and oxyhemoglobin differ substantially from one another. The detected light signal detected by the system comprises an alternating-current (AC) component and a direct-current (DC) component for each of the respective light sources. The components of each of the detected signals are used to form a voltage amplitude ratio. This ratio is then correlated with an oxygen saturation reference curve to obtain an indication of the oxygen saturation of the patient's arterial blood.

The method and apparatus of the present invention overcomes the difficulties associated with trends in the pulse waveforms by processing the pulse signals to compensate for the effects of the trends. The pulse amplitude signals used in the calculation of blood oxygen saturation are purged of the effects of upward or downward trends and, therefore, the accuracy of the blood oxygen saturation calculation is significantly increased. The trend correction method implemented in the present invention comprises the following steps: First, the diastolic-to-systolic time intervals and median pulse amplitudes are calculated for the current pulse signal and for the previous pulse signal. Next, a trend slope factor is calculated as the ratio of a first quantity, calculated as the difference between the current median signal and the previous median signal, and a second quantity, calculated as the difference between the current diastolic-to-systolic time interval and the previous diastolic-to-systolic time interval. Corrected systolic and diastolic signals are then calculated by subtracting a trend quantity from the measured values, said trend quantity being the product of the trend slope factor multiplied by the diastolic-to-systolic time interval.

DETAILED DESCRIPTION OF THE PREFERRED EMBODIMENT

Figure 1:
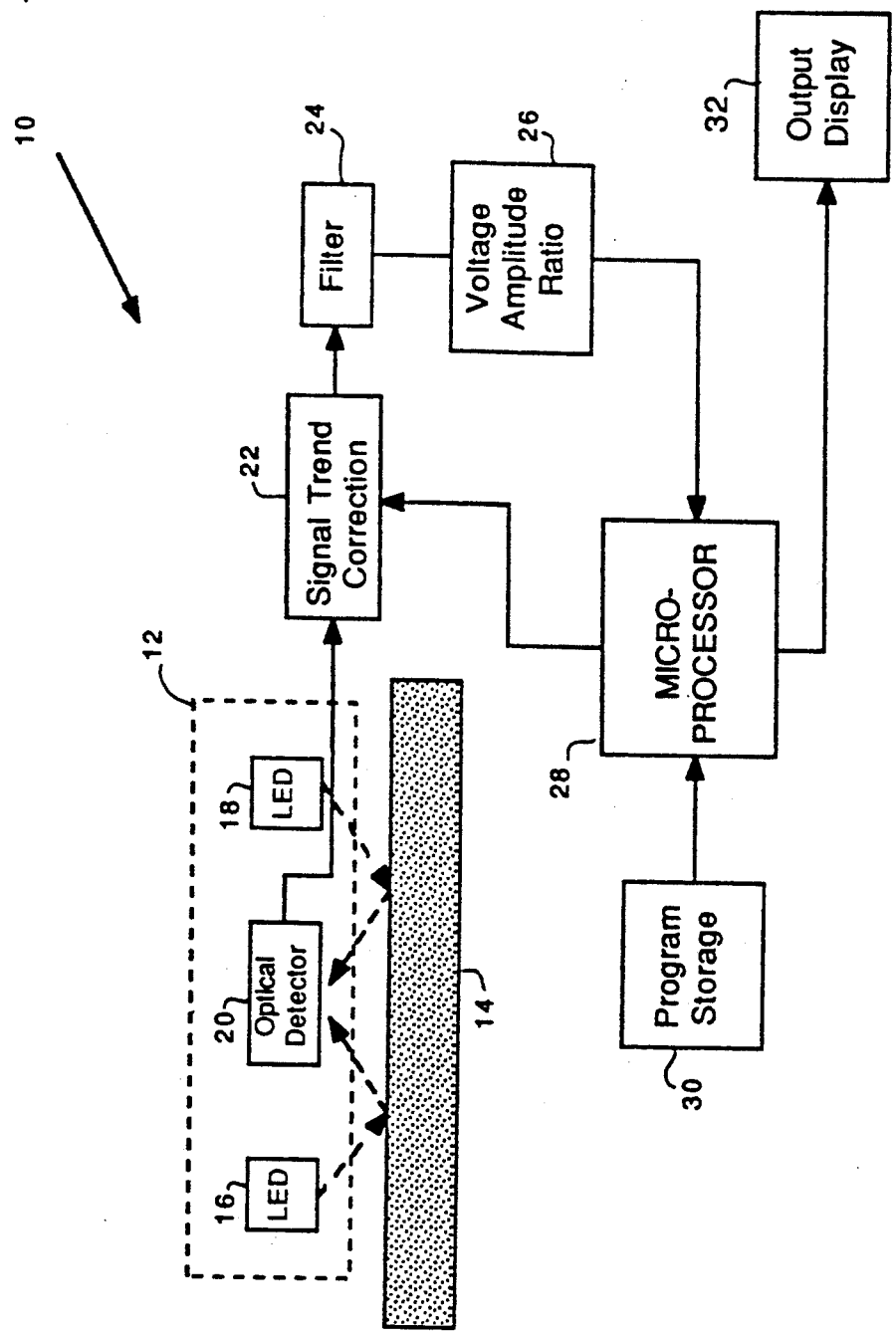
FIG. 1 is a schematic block diagram of a simplified embodiment of the noninvasive blood oxygen saturation monitoring system of the present invention.

Referring to the drawings in more detail, and to FIG. 1 in particular, the noninvasive monitoring system 10 of the present invention is shown in its preferred embodiment. A monitoring probe 12 is positioned over a portion of the patient's tissue 14 such that light produced by two light emitting diodes (LED) 16 and 18 will be reflected by arterial blood in the tissue and detected by a photodetector 20. In the preferred embodiment, the LED 16 emits light having a wavelength of 660 nm (red) and the LED 18 emits light having a wavelength of 900 nm (infrared). However, the invention is not intended to be limited to any specific wavelength of light produced by the above mentioned LEDs. Proper operation of the invention requires only that one of the sources of light have a wavelength at which the absorption coefficients of hemoglobin and oxyhemoglobin differ substantially from one another. The output of the photodetector 20 will be an electrical signal representing a combination of direct-current (DC) and alternating-current (AC) components of the light reflected by the arterial blood in the tissue 14.

Figure 2A:
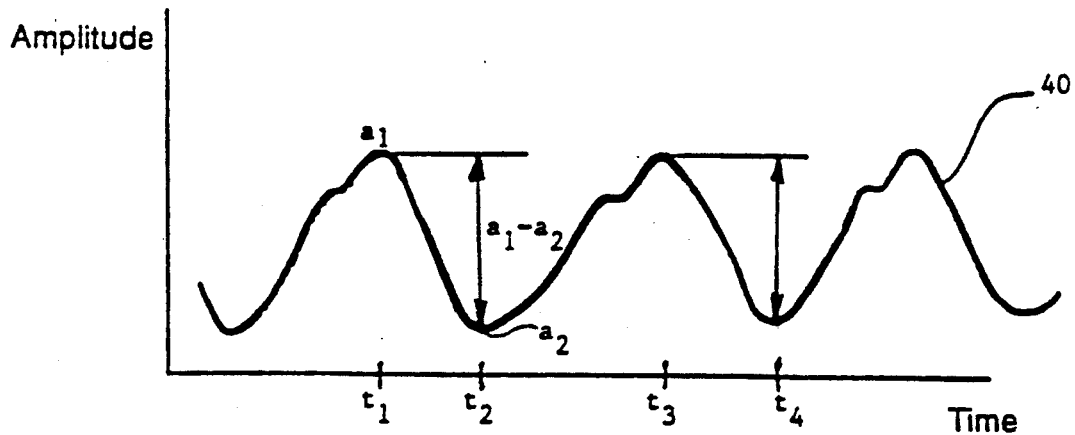
FIG. 2a is a graphical representation of pulse waveform detected by the optical sensor of the reflectance oximeter system of the present invention.
Figure 2B:
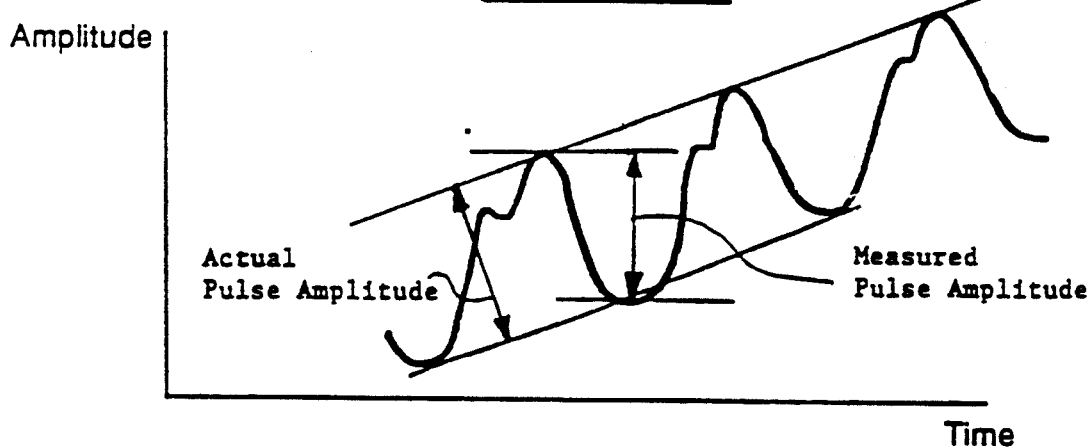
FIG. 2b is a graphical representation of pulse waveform having an upward trend.
Figure 2C:
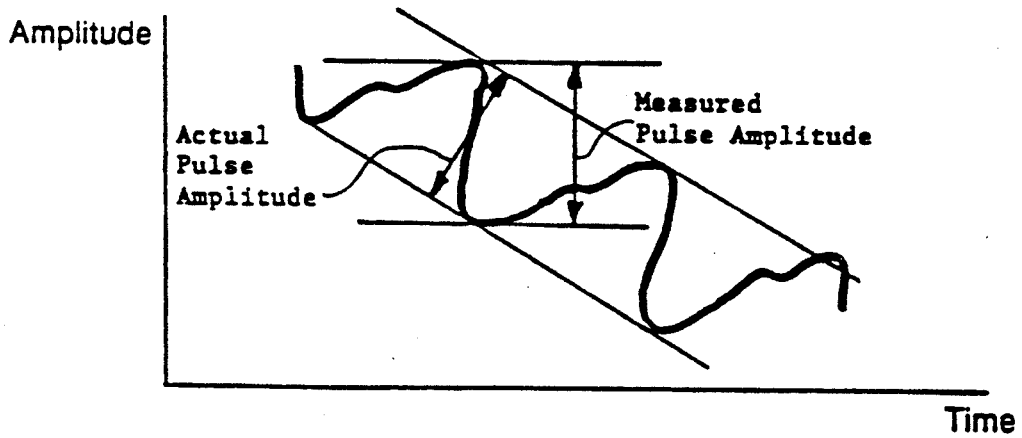
FIG. 2c is a graphical representation of pulse waveform having a downward trend.

FIG. 2a is a graphical representation of a typical pulse waveform output signal produced by the photodetector 20 for each of the wavelengths of reflected light. FIGS. 2b and 2c illustrate pulse amplitude signals having upward and downward trends, respectively. As was discussed above, such trends can lead to inaccuracies in the measurement of the pulse amplitudes and thus in the measurement of the blood oxygen saturation of the tissue. In the present invention, these trends in the signals are compensated by a signal trend correction system 22, which implements a trend correction method described in greater detail below.

The corrected output signal from the optical detector 20 is processed by an appropriate filter 24 to produce separate signals corresponding to the AC and DC voltage components of each of the wavelengths of incident light. These AC and DC voltage signals for each wavelength are then processed by a voltage amplitude ratio circuit 26 to provide an output signal corresponding to the ratio of the AC/DC portions of the reflected signals. The AC/DC ratios at each wavelength are then used to form a final composite ratio. The final voltage amplitude ratio output signal is provided to a microprocessor 28 which calculates the oxygen saturation in accordance with an algorithm and a data reference curve stored in program storage 30. The calculated oxygen saturation is then displayed on an appropriate display device 32.

Referring to FIG. 2a, a reference system for determining pulse amplitudes will now be discussed. FIG. 2a is a graphical illustration of a typical pulse amplitude signal 40 detected by optical detector 20. Diastolic time is defined as the time at which the light reflected from the tissue is at its local maximum level as detected by the optical detector 20. Likewise, systolic time is defined as the time at which the light reflected from the tissue is at its local minimum level.

The pulse detection window (the search window used to find the minimum and maximum of a pulse) is the expected diastolic-to-systolic time of the next pulse, e.g., t3-t4 shown in FIG. 2a. Ideally, the monitoring system should not identify a waveform as a pulse until both a maximum and a minimum level of the pulse detection channel's waveform have been identified and the amount of time between the identification of the maximum, diastolic time, and the current data sample period is at least as large as the pulse detection window. This is done to ensure that the minimum level actually occurred at systolic time and was not the result of an artifact such as motion or electrical noise. If the pulse detection window is too small, the system may incorrectly identify an artifact as a pulse. Also, if the pulse detection window is too large, more than one pulse may occur in the window and and the system will fail to identify any pulse.

In many prior systems, the diastolic-to-systolic time of the most recent pulse (i.e., the amount of time between the occurrence of diastole and the occurrence of systole) is used to calculate a pulse detection window for the next pulse. For example, in FIG. 2a, the first time interval t1-t2 would be used to predict the next time interval, e.g., t3-t4, which is the expected diastolic-to-systolic time of the next pulse. As a result, if the diastolic or systolic time is incorrectly identified in the first interval, the pulse detection window for the next pulse will be erroneously predicted and may cause the next pulse to be missed or identified incorrectly.

In addition, prior pulse detection techniques in which the diastolic-to-systolic time of the most recently identified pulse is used for the pulse detection window of the next pulse are also very susceptible to signal artifacts. If an artifact is mistakenly identified as a pulse, its incorrect diastolic-to-systolic time is used as the new pulse detection window. This tends to cause the system to lock onto artifacts and reject pulses. In the preferred embodiment of the present invention, an average of the last four diastolic-to-systolic times is used as the period for the new pulse detection window.

The pulse amplitude is the AC component of the waveform detected by the optical sensor 20. For example, the pulse amplitude during time interval t1-t2 in FIG. 2a is a1-a2. In the system of the present invention, the minimum and maximum pulse amplitudes are limits which are calculated using the pulse amplitude information from one or more previously detected pulses. The system will not identify a waveform as a pulse unless the amplitude of the pulse waveform is between the maximum and minimum pulse amplitudes. This is done to prevent artifacts which have the correct timing, or pulses which have been corrupted by artifacts, from being accepted as pulses. It is apparent that the calculation of the minimum and maximum pulse amplitudes affects the correct detection of pulses. If the minimum and maximum pulse amplitudes are too close together, many good pulses may be missed because their pulse amplitudes are not within the specified range. Also, if the minimum and maximum pulse amplitudes are too far apart, false or corrupted pulses may be accepted when they should have been rejected.

Many prior systems tend to reject valid pulses because the range specified by the minimum and maximum pulse amplitudes is too narrow. Also, an invalid pulse is sometimes mistakenly identified as a pulse and used to calculate the minimum and maximum pulse amplitudes for the next pulse. The present system solves these problems by using an average of the last four pulse amplitudes to calculate the minimum and maximum pulse amplitude for the next pulse and by increasing the range specified by the minimum and maximum pulse amplitudes using the following relationships:

Minimum Pulse Amplitude = Average Pulse Amplitude /3.0

Maximum Pulse Amplitude = Average Pulse Amplitude *3.0

The scale factor of 3.0 used in the above equations was selected after comparing data obtained using several scale factors in the range of 1.5 to 5.0. Smaller values for the scale factor tended to reject pulses, and larger values for the scale factor tended to cause the system to accept invalid pulses. In general, a scale of approximately 3.0 has been found to result in the largest percentage of valid pulses and the smallest percentage of invalid pulses.

In the preferred embodiment of the invention, blood oxygen saturation ($SaO_2$) is calculated using an algorithm stored in program storage 30 which relates $SaO_2$ to ratios of the reflected intensities of two wavelengths of light. The empirical formula is as follows:

$$SaO_2 = A + B*[(\text{pulse amplitude/median signal})_{red}/(\text{pulse amplitude/median signal})_{infrared}]$$

where: A and B are empirical constants.

Empirical constant A can be mathematically derived, and examples of such a derivation are disclosed in U.S. Pat. No. 4,714,080 to Edgar, Jr. et al., and in U.S. Pat. No. 4,796,636 to Branstetter et al., the disclosure of which are herein incorporated by reference. Specifically, A can be calculated using the equation below:

$$A = [(K_B W_{Dr})/]35 H_B K_{Dr} (W_{Or} - W_{Rr}))] + [W_{Rr}/(W_{Rr} - W_{Or})]$$

Where:

$K_B$ = Scattering due to blood;
$K_{Dr}$ = Scattering due to tissue and blood at diastolic pulse for wavelength 660 nm;
$H_B$ = Fraction of blood volume containing hemoglobin;
$W_{Dr}$ = Absorption due to tissue and blood at diastolic pulse for wavelength 660 nm;
$W_{Rr}$ = Absorption coefficient for reduced hemoglobin for wavelength 660 nm; and
$W_{Or}$ = Absorption coefficient for oxygenated hemoglobin for wavelength 660 nm.

It has been shown experimentally that the first term is very small in magnitude and can be ignored without causing significant error in the calculation of A. The second term is composed of the absorption coefficients for oxygenated and reduced hemoglobin at a known wavelength, for example 660 nm (red). These values are known constants which are related to the wavelength of light used to illuminate the blood. Therefore, A can be calculated by substituting the values of these absorption coefficients in the second term. As an example, for light at 660 nm, the value for $W_{Rr}$ will be 1.732 and the value for $W_{Or}$ will be 0.211. BY substituting these values in the second term, A is calculated to be 112%.

Empirical constant B is determined empirically by calibrating the system to one or more patients having known oxygen saturation levels, e.g. 98%.

In another embodiment, the empirical formula for calculating oxygen saturation may be based on the average pulse signal rather than the median pulse signal as shown above. Calculations based on the average signal also provide accurate results, but are less desirable with respect to implementing an averaging algorithm in the microprocessor 28.

Generally, the pulse amplitude detected by the optical sensor 20 is less than one percent of the total reflected signal intensity. It is readily apparent, therefore, that even minor inaccuracies in the measurement of pulse amplitudes will cause the calculation of $SaO_2$ to be incorrect. Errors in the measurement of pulse amplitudes can occur when the levels of the waveforms trend upward or downward. When the median (or average) signal of the oximetry waveforms trend upward, the pulse amplitudes of the waveforms tend to be artificially small. This is illustrated in FIG. 2b, where the actual pulse amplitude is shown to be larger than the measured pulse amplitude. Likewise, when the median signal of the oximetry waveforms trend downward, the pulse amplitudes of the waveforms tend to be artificially large. This phenomenon is illustrated in FIG. 2c.

When the levels of the waveforms trend upward or downward, most prior art systems measure the pulse amplitudes of each of the waveforms incorrectly. As a result, the calculation of $SaO_2$ for these pulses is incorrect. The system of the present invention overcomes the above discussed difficulties by compensating for the upward or downward trend in the waveform. In the preferred embodiment, this is done by correcting the signal levels measured at diastolic and systolic times for each waveform as follows:

First, the average time during each interval is calculated as

Average time = (Systolic time + Diastolic time)/2

Next, the Median signal during each interval is calculated as:

Median signal = (Systolic Level + Diastolic Level)/2

From the above relationships, the Trend Slope can be calculated as:

$$\text{Trend Slope} = \frac{(\text{Current Median Signal} - \text{Previous Median Signal})}{(\text{Current Average time} - \text{Previous Average time})}$$

The corrected systolic and diastolic levels can now be determined as:

Systolic Level$_{correct}$ = Systolic Level$_{measured}$ − (Trend Slope * Diastolic-to-Systolic time)

Diastolic Level$_{correct}$ = Diastolic Level$_{measured}$ + (Trend Slope * Diastolic-to-Systolic time)

Finally, the corrected pulse amplitude can now be determined as:

Pulse Amplitude$_{correct}$ = Diastolic Level$_{correct}$ − Systolic Level$_{correct}$ The detrending procedure outlined above improves the measurement of the pulse amplitude for each waveform and allows the monitoring system of the present invention to provide significantly improved measurements of blood oxygen saturation. It is noted, however, that if trending in the waveforms is very rapid (lasting only two or three pulses), detrending as described above may overcompensate the measured pulse amplitude.

One method for protecting against such overcompensation is to revert to the "non-detrended" diastolic and systolic levels for each waveform if detrending causes the pulse amplitude for the pulse to be rejected when the non-detrended pulse amplitude would have been accepted. For example, if the detrended pulse amplitude exceeds the maximum and minimum pulse amplitude levels whereas the non-detrended pulse amplitude does not, $SaO_2$ calculations would be based on the non-detrended pulse amplitude.

In other embodiments, trend compensation techniques may be based not only on present and previous pulse information, but also on information from additional preceding and/or subsequent pulses. For example, initial individual trend slopes may be calculated for the present pulse (n) with respect to both a preceding pulse (n−1), and a subsequent pulse (n+1). These individual slopes may then be averaged or otherwise compared in order to arrive at the overall trend slope value from which the corrected pulse amplitude is determined. Another embodiment may determine the trend slope based on information from a plurality of pulses utilizing various curve fitting techniques.

Although the method and apparatus of the present invention has been described in connection with the preferred embodiment, it is not intended to be limited to the specific form set forth herein, but on the contrary, it is intended to cover such alternatives, modifications and equivalents within the spirit and scope of the invention as defined by the appended claims.

What is claimed is:

1. An oximeter for measuring the oxygen saturation of blood comprising:
   first and second sources of electromagnetic radiation having first and second wavelengths of radiation, respectively, for illuminating a sample of said blood;
   a sensor for detecting electromagnetic radiation generated by said first and second sources which has illuminated said blood sample and for producing electrical signals corresponding to the intensity of the detected electromagnetic radiation at each of said first and second wavelengths, each of radiation at each of said first and second wavelengths, each of said electrical signals having an AC pulsatile component and a DC component;
   a signal correction circuit for modifying said AC pulsatile component of each of said electrical signals to remove upward and downward trend effects therefrom;
   a signal processor for combining said modified AC pulsatile components and said DC components of said electrical signals for producing a measurement signal related to the oxygen saturation of said blood sample.

2. The oximeter of claim 1 further comprising a display, and said signal processor comprises means for comparing said measurement signal with a reference curve representative of blood oxygen saturation characteristics bored in an electronic storage memory, and for controlling said display in dependence on said comparison to provide an indication of the measured oxygen saturation.

3. The oximeter of claim 1 wherein each of said AC pulsatile components comprises pulses having maximum and minimum signal levels defined by a diastolic-to-systolic time interval between a diastolic time at which the detected light intensities are at their respective local maximum level, and a systolic time at which the detected light intensities are at their respective local minimum level; and said signal correction circuit comprises:
   means for determining, for at least one of said electrical signals, a current pulse time interval and a current pulse median amplitude representing, respectively, the average diastolic-to-systolic time interval and the median of the difference between the systolic and diastolic signal levels for at least one of the most recent pulses; and a prior pulse time interval and a prior pulse median amplitude representing, respectively, the average diastolic-to systolic time interval and the median of the difference between the systolic and diastolic signal levels for at least one previous pulse;
   means for determining a trend slope factor corresponding to the ratio of a first quantity, comprising the difference between said current and said previous pulse median amplitudes, and a second quantity, comprising the difference between said current and said previous pulse time intervals;
   means for adjusting the measured systolic and diastolic signal levels of the current pulse for each of said electrical signals according to a trend factor corresponding to the product of said trend slope factor and the diastolic-to-systolic time interval of the current pulse, thereby producing a detrended current pulse.

4. The oximeter of claim 3 wherein said current and said prior pulse diastolic-to-systolic time intervals and median amplitudes are each averaged parameters derived from a plurality of pulses.

5. The oximeter of claim 3 further comprising means for comparing the amplitude, defined as the difference between the diastolic and systolic signal levels of a pulse, of a detrended current pulse with predetermined maximum and minimum amplitude limits, and for selecting one of the detrended current pulse and the current pulse from which the detrended pulse was derived for further processing in dependence on said amplitude comparison.

6. The oximeter of claim 3 wherein said signal correction circuit comprises means for rejecting a detected pulse in said AC components for further processing which has a pulse amplitude, defined as the difference between the diastolic and systolic signal levels of the pulse, which is outside a range limit defined by maximum and minimum pulse amplitude limits determined based on the pulse amplitude of at least one previously detected pulse.

7. The oximeter of claim 6 wherein said maximum pulse amplitude limit corresponds to an average pulse amplitude of a plurality of previous pulses divided by a scale factor; and said minimum pulse amplitude limit corresponds to said average pulse amplitude multiplied by said scale factor.

8. The oximeter of claim 7 wherein said scale factor is approximately equal to three.

9. The oximeter of claim 3 further comprising:
   pulse detection window means for rejecting detected pulses in said AC components for further processing which do not have a diastolic-to-systolic time interval which exceeds the duration of a pulse detection window determined based on the diastolic-to-systolic time interval of at least one previous unrejected pulses.

10. The oximeter of claim 9 wherein the duration of said pulse detection window is based on an average of the diastolic-to-systolic time intervals for a plurality of previous unrejected pulses.

11. The oximeter of claim 1 further comparison noninvasive monitoring probe housing said first and second sources of electromagnetic radiation and said sensor, said monitoring prove being positionable over a portion of a patient's tissue such that said electromagnetic radiation illuminates a sample of the patient's arterial blood in tissue, and said sensor detects electromagnetic radiation reflected from said blood sample.

12. Signal generating and conditioning apparatus for use in measurement of the oxygen saturation of arterial blood in tissue, said apparatus comprising:

first and second sources of electromagnetic radiation having first and second wavelengths of radiation, respectively, for illuminating a sample of said blood;

a sensor for detecting electromagnetic radiation generated by said first and second sources which has illuminated said blood sample and for producing electrical signals corresponding to the intensity of the detected electromagnetic radiation at each of said first and second wavelengths, each of said electrical signals having an AC pulsatile component and a DC component; and a signal correction circuit for modifying said AC pulsatile component of each of said electrical signals to remove upward and downward trend effects therefrom.

13. The signal generating and conditioning apparatus of claim 12 wherein said each of said AC pulsatile components comprises pulses having maximum and minimum signal levels defined by a diastolic-to-systolic time interval between a diastolic time at which the detected light intensities are at their respective local maximum level, and a systolic time at which the detected light intensities are at their respective local minimum level; and said signal correction circuit comprises:

means for determining, for at least one of said electrical signals, a current pulse time interval and a current pulse median amplitude representing, respectively, the average diastolic-to-systolic time interval and the median of the difference between the systolic and diastolic signal levels for at least one of the most recent pulses; and a prior pulse time interval and a prior pulse median amplitude representing, respectively, the average diastolic-to systolic time interval and the median of the difference between the systolic and diastolic signal levels for at least one previous pulse;

means for determining a trend slope factor corresponding to the ratio of a first quantity, comprising the difference between said current and said previous pulse median amplitudes, and a second quantity, comprising the difference between said current and said previous pulse time intervals;

means for adjusting the measured systolic and diastolic signal levels of the current pulse for each of said electrical signals according to a trend factor corresponding to the product of said trend slope factor and the diastolic-to-systolic time interval of the current pulse, thereby producing a detrended current pulse.

14. The signal generating and conditioning apparatus of claim 13 further comprising means for comparing the amplitude, defined as the difference between the diastolic and systolic signal levels of the pulse, of a detrended current pulse with predetermined maximum and minimum amplitude limits, and for selecting one of the detrended current pulse and the current pulse from which the detrended pulse was derived for further processing in dependence on said amplitude comparison.

15. The signal generating and conditioning apparatus of claim 14 wherein said signal correction circuit comprises means for rejecting a detected pulse in said AC components for further processing which has a pulse amplitude which is outside a range limit defined by maximum and minimum pulse amplitude limits determined based on the pulse amplitude of at least one previously detected pulse.

16. The signal generating and conditioning apparatus of claim 15 further comprising pulse detection window means for rejecting detected pulses in said AC components for further processing which do not have a diastolic-to-systolic time interval which exceeds the duration of a pulse detection window determined based on the diastolic-to-systolic time interval of at least one previous unrejected pulses.

* * * * *